(12) United States Patent
Erben et al.

(10) Patent No.: US 7,989,488 B2
(45) Date of Patent: Aug. 2, 2011

(54) COMPOSITIONS AND METHODS FOR STORING HOLOGRAPHIC DATA

(75) Inventors: Christoph Georg Erben, Los Gatos, CA (US); Michael Jeffrey Mclaughlin, Richmond, VA (US); Kathryn Lynn Longley, Saratoga Springs, NY (US); Shantaram Narayan Naik, Bangalore (IN); Mahesh Kisan Chaudhari, Jalgaon (IN); Jyoti Balkrishna Shet, Ponda (IN); Varadarajan Sundararaman, Chennai (IN); Yogendrasinh Bharatsinh Chauhan, Vadodara (IN); Gary Charles Davis, Albany, NY (US); Sumeet Jain, Niskayuna, NY (US); Moitreyee Sinha, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 921 days.

(21) Appl. No.: 11/863,385

(22) Filed: Sep. 28, 2007

(65) Prior Publication Data

US 2009/0082580 A1  Mar. 26, 2009

Related U.S. Application Data

(60) Provisional application No. 60/974,868, filed on Sep. 25, 2007.

(51) Int. Cl.
*A61K 31/381* (2006.01)
*C07D 333/12* (2006.01)

(52) U.S. Cl. .......................... 514/444; 549/74
(58) Field of Classification Search .............. 549/74; 514/444
See application file for complete search history.

(56) References Cited

U.S. PATENT DOCUMENTS

| | | | |
|---|---|---|---|
| 3,390,133 A | 6/1968 | Breslow | |
| 3,418,285 A | 12/1968 | Breslow | |
| 3,850,633 A | 11/1974 | Moraw et al. | |
| 4,247,474 A | 1/1981 | Breslow | |
| 6,489,065 B1 | 12/2002 | Dhal et al. | |
| 7,022,460 B2 | 4/2006 | Berneth et al. | |
| 7,102,802 B1 | 9/2006 | Erben et al. | |
| 2005/0136333 A1 | 6/2005 | Lawrence et al. | |
| 2006/0073392 A1 | 4/2006 | Erben et al. | |
| 2007/0127329 A1 | 6/2007 | Erben et al. | |

FOREIGN PATENT DOCUMENTS

WO  2004059389 A3  9/2004

OTHER PUBLICATIONS

King, Med. Chem. Principle and Practice (1994), pp. 206-208.*

* cited by examiner

*Primary Examiner* — Taofiq A Solola
(74) *Attorney, Agent, or Firm* — Richard A. DeCristofaro

(57) ABSTRACT

In one aspect, the present invention provides a novel thiophene-containing polynitrone compound having structure (II)

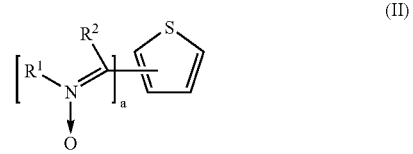

(II)

wherein $R^1$ is independently at each occurrence a $C_1$-$C_{20}$ aliphatic radical, a $C_3$-$C_{20}$ cycloaliphatic radical, or a $C_2$-$C_{30}$ aromatic radical; $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; and "a" is an integer from 2 to 4.

20 Claims, No Drawings

COMPOSITIONS AND METHODS FOR STORING HOLOGRAPHIC DATA

RELATED APPLICATIONS

This non-provisional application is related to U.S. provisional application having Ser. No. 60/974,868, filed Sep. 25, 2007.

BACKGROUND

The invention relates to methods for storing holographic data. Further, the present disclosure relates to holographic data storage media and articles, which are derived from these methods. In addition the present disclosure relates to thiophene-containing polynitrones dyes.

Holographic storage is the storage of data in the form of holograms, which are images of three dimensional interference patterns created by the intersection of two beams of light, in a photosensitive medium. The superposition of a signal beam, which contains digitally encoded data, and a reference beam forms an interference pattern within the volume of the medium resulting in a chemical reaction that changes or modulates the refractive index of the medium. This modulation serves to record as the hologram both the intensity and phase information from the signal. The hologram can later be retrieved by exposing the storage medium to the reference beam alone, which interacts with the stored holographic data to generate a reconstructed signal beam proportional to the initial signal beam used to store the holographic image. Thus, in holographic data storage, data is stored throughout the volume of the medium via three dimensional interference patterns.

Each hologram may contain anywhere from one to $1\times10^6$ or more bits of data. One distinct advantage of holographic storage over surface-based storage formats, including CDs or DVDs, is that a large number of holograms may be stored in an overlapping manner in the same volume of the photosensitive medium using a multiplexing technique, such as by varying the signal and/or reference beam angle, wavelength, or medium position. However, a major impediment towards the realization of holographic storage as a viable technique has been the development of a reliable and economically feasible storage medium.

Early holographic storage media employed inorganic photo-refractive crystals, such as doped or un-doped lithium niobate ($LiNbO_3$), in which incident light creates refractive index changes. These refractive index changes are due to the photo-induced creation and subsequent trapping of electrons leading to an induced internal electric field that ultimately modifies the refractive index through a linear electro-optic effect. However, $LiNbO_3$ is expensive, exhibits relatively poor efficiency, fades over time, and requires thick crystals to observe any significant index changes.

Therefore, there is a need for improved holographic data storage methods and materials through which enhanced holographic data storage capacities can be achieved. Further, there is also a need for methods to enhance the lifetime of the stored holographic data, such that for example, the data is not erased thermally, or when ambient light is incident on the data storage medium, or during read-out.

BRIEF DESCRIPTION

In one aspect, the present invention provides a method for storing holographic data, said method comprising:

(A) providing a holographic storage medium comprising an optically transparent substrate, said optically transparent substrate comprising a photochemically active dye having at least two nitrone groups; and (B) irradiating the optically transparent substrate with a holographic interference pattern, wherein the pattern has a first wavelength and an intensity both sufficient to convert, within a volume element of the substrate, at least some of the photochemically active dye into a photo-product, and producing within the irradiated volume element concentration variations of the photo-product corresponding to the holographic interference pattern, thereby producing an optically readable datum corresponding to the volume element.

In another aspect, the present invention provides a method for storing holographic data, said method comprising:

(A) providing a holographic storage medium comprising an optically transparent substrate, said optically transparent substrate comprising a photochemically active dye having structure (I)

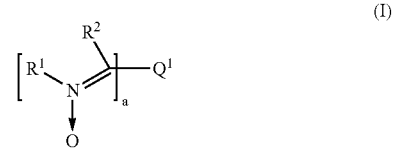

(I)

wherein $R^1$ is independently at each occurrence a $C_1$-$C_{20}$ aliphatic radical, a $C_3$-$C_{20}$ cycloaliphatic radical, or a $C_2$-$C_{30}$ aromatic radical; $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; $Q^1$ is a $C_1$-$C_{20}$ aliphatic radical, a $C_3$-$C_{20}$ cycloaliphatic radical, or a $C_2$-$C_{30}$ aromatic radical, or a polymer chain; and "a" is an integer from 2 to 100; and (B) irradiating the optically transparent substrate with a holographic interference pattern, wherein the pattern has a first wavelength and an intensity both sufficient to convert, within a volume element of the substrate, at least some of the photochemically active dye into a photo-product, and producing within the irradiated volume element concentration variations of the photo-product corresponding to the holographic interference pattern, thereby producing an optically readable datum corresponding to the volume element.

In still yet another aspect, the present invention provides a method for storing holographic data, said method comprising:

(A) providing a holographic storage medium comprising an optically transparent substrate, said optically transparent substrate comprising a photochemically active dye having structure (II)

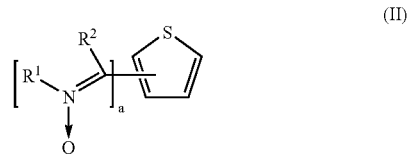

(II)

wherein $R^1$ is independently at each occurrence a $C_1$-$C_{20}$ aliphatic radical, a $C_3$-$C_{20}$ cycloaliphatic radical, or a $C_2$-$C_{30}$ aromatic radical; $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; and "a" is an integer from 2 to 4, wherein the dye is present in an amount from about 0.1 weight percent to about 10 weight percent; and (B) irradiating the optically transparent substrate with a holographic interference pattern, wherein the pattern has a first wavelength and an intensity both sufficient to convert, within a volume element of the substrate, at least some of the photochemically active dye into a photo-product, and producing within the irradiated volume element concentration variations of the photo-product corresponding to the holographic interference pattern, thereby producing an optically readable datum corresponding to the volume element, and wherein the first wavelength is about 500 nm.

In yet another embodiment, the present invention provides a novel thiophene-containing polynitrone compound having structure (II).

These and other features, aspects, and advantages of the present invention may be understood more readily by reference to the following detailed description.

DETAILED DESCRIPTION

In the following specification and the claims, which follow, reference will be made to a number of terms, which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "solvent" can refer to a single solvent or a mixture of solvents.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having $4n+2$ "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical, which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC(CF$_3$)$_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms, which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylclooct-1-yl, 2-chlorodifluoromethylcyclohex-1-yl, hexafluoroisopropylidene-2,2-bis(cyclohex-4-yl) (i.e., —$C_6H_{10}C(CF_3)_2C_6H_{10}O$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., $CH_3CHBrCH_2C_6H_{10}O$—), and the like. Further examples of cycloaliphatic radicals include 4-allyloxycyclohex-1-yl, 4-aminocyclohex-1-yl (i.e., $H_2C_6H_{10}$—), 4-aminocarbonylcyclopent-1-yl (i.e., $NH_2COC_5H_8$—), 4-acetyloxycyclohex-1-yl, 2,2-dicyanoisopropylidenebis(cyclohex-4-yloxy) (i.e., —$OC_6H_{10}C(CN)_2C_6H_{10}O$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}O$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl (i.e., $NO_2CH_2C_6H_{10}$—), 3-trimethylsilylcyclohex-1-yl, 2-t-butyldimethylsilylcyclopent-1-yl, 4-trimethoxysilylethylcyclohex-1-yl (e.g., $(CH_3O)_3SiCH_2CH_2C_6H_{10}$—), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e., —CHO), hexyl, hexamethylene, hydroxymethyl (i.e., —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

As defined herein, the term "optically transparent" as applied to an optically transparent substrate or an optically transparent plastic material means that the substrate or plastic material has an absorbance of less than 1. That is, at least 10 percent of incident light is transmitted through the material at least one wavelength in a range between about 300 nanometers and about 1500 nanometers. For example, when configured as a film having a thickness suitable for use in holographic data storage said film exhibits an absorbance of less than 1 at least one wavelength in a range between about 300 nanometers and about 1500 nanometers.

As used herein, the terms "photochemically reactive" and "photochemically active" have the same meaning and are interchangeable terms.

As defined herein, the term "volume element" means a three dimensional portion of a total volume.

As defined herein, the term "optically readable datum" can be understood as a datum that is stored as a hologram patterned within one or more volume elements of an optically transparent substrate.

As noted, holographic data storage relies upon the introduction of localized variations in the refractive index of the optically transparent substrate comprising the photochemically active dye as a means of storing holograms. The refractive index within an individual volume element of the optically transparent substrate may be constant throughout the volume element, as in the case of a volume element that has not been exposed to electromagnetic radiation, or in the case of a volume element in which the photochemically active dye has been reacted to the same degree throughout the volume element. It is believed that most volume elements that have been exposed to electromagnetic radiation during the holographic data writing process will contain a complex holographic pattern, and as such, the refractive index within the volume element will vary across the volume element. In instances in which the refractive index within the volume element varies across the volume element, it is convenient to regard the volume element as having an "average refractive index" which may be compared to the refractive index of the corresponding volume element prior to irradiation. Thus, in one embodiment an optically readable datum comprises at least one volume element having a refractive index that is different from a (the) corresponding volume element of the optically transparent substrate prior to irradiation. Data storage is achieved by locally changing the refractive index of the data storage medium in a graded fashion (continuous sinusoidal variations), rather than discrete steps, and then using the induced changes as diffractive optical elements.

In one embodiment of the invention, a holographic storage medium comprising an optically transparent substrate is provided. The optically transparent substrate may be made of materials possessing sufficient optical quality such as, low scatter, low birefringence, and negligible losses at the wavelengths of interest, to render the data stored in the holographic storage medium readable. Generally, plastic materials that exhibit these properties may be used as the substrate. However, the plastic materials should be capable of withstanding the particular processing parameters employed (e.g., inclusion of the dye, exposure to a sensitizing solvent and application of any coating or subsequent layers, and molding it into a final format) and subsequent storage conditions. In one embodiment, the optically transparent plastic materials may comprise organic polymers such as, for example, oligomers, polymers, dendrimers, ionomers, copolymers such as block copolymers, random copolymers, graft copolymers, star block copolymers, and the like, or a combination comprising at least one of the foregoing polymers. In one embodiment, the optically transparent substrate comprises a polycarbonate.

The photochemically active dye is one which renders the optically transparent substrate capable of having holograms "written" into it at a first wavelength. And further, the photochemically active dye should be such that a hologram having been "written" into the optically transparent substrate at a first wavelength is not erased when the hologram is "read". It is desirable to use dyes that enable "writing" of the holographic interference pattern into the optically transparent substrate at a wavelength in a range from about 300 nm to about 800 nm.

In one embodiment, the photochemically active dye has an optical absorption resonance characterized by a center wavelength associated with the maximum absorption and a spectral width (full width at half of the maximum, FWHM) of less than 500 nanometers. Typically, the photochemically active dyes undergo a light induced chemical reaction when exposed to light with a wavelength within the absorption range to form at least one photo-product. This reaction can be a photo-decomposition reaction, such as oxidation, reduction, or bond breaking to form smaller constituents, or a molecular rearrangement, such as a sigmatropic rearrangement, or addition reactions including pericyclic cycloadditions. Thus in an embodiment, data storage in the form of holograms is achieved wherein the photo-product is patterned within the optically transparent substrate to provide the at least one optically readable datum.

In an embodiment, the photochemically active dye is a compound comprising at least two nitrone groups having a structure (I)

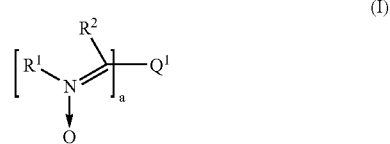

wherein $R^1$ is independently at each occurrence a $C_1$-$C_{20}$ aliphatic radical, a $C_3$-$C_{20}$ cycloaliphatic radical, or a $C_2$-$C_{30}$ aromatic radical; $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; $Q^1$ is a $C_1$-$C_{20}$ aliphatic radical, a $C_3$-$C_{20}$ cycloaliphatic radical, or a $C_2$-$C_{30}$ aromatic radical, or a polymer chain; and "a" is an integer from 2 to 100.

Representative polynitrone compounds encompassed by generic structure (I) are illustrated in Table I. One of ordinary skill in the art will appreciate the relationship between generic structure (I) and the individual structures of Entries 1a-1f of Table I.

TABLE I

| | Compounds Exemplifying The Photochemically Active Dye Having . . . Structure (I) | |
|---|---|---|
| Example | Structure | Comment |
| 1a | 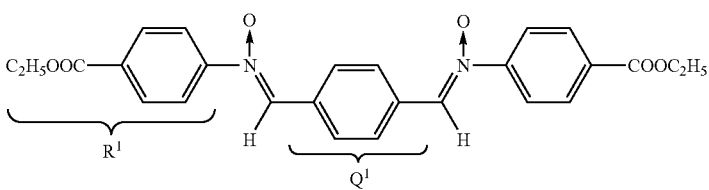 | $R^2$ = hydrogen; a = 2. |
| 1b | 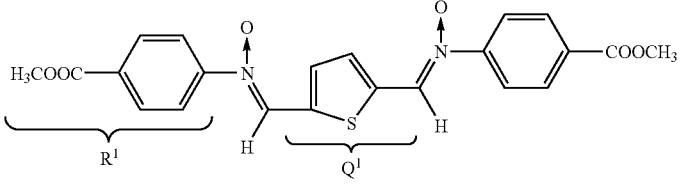 | $R^2$ = hydrogen; a = 2. |
| 1c | 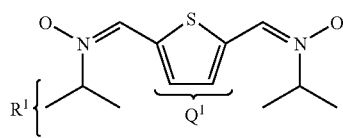 | $R^2$ = hydrogen; a = 2. |

TABLE I-continued

Compounds Exemplifying The Photochemically Active Dye Having . . . Structure (I)

| Example | Structure | Comment |
|---|---|---|
| 1d | 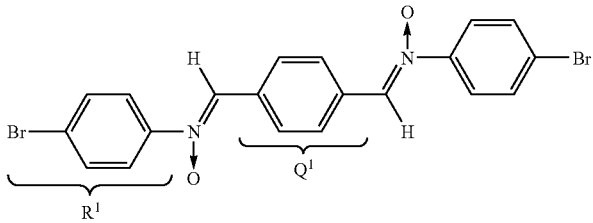 | $R^2$ = hydrogen; a = 2. |
| 1e | 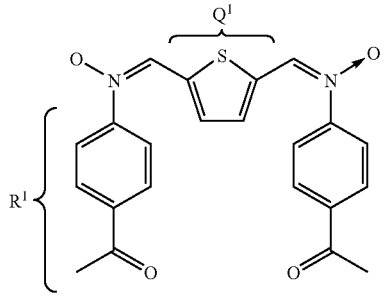 | $R^2$ = hydrogen; a = 2. |
| 1f | 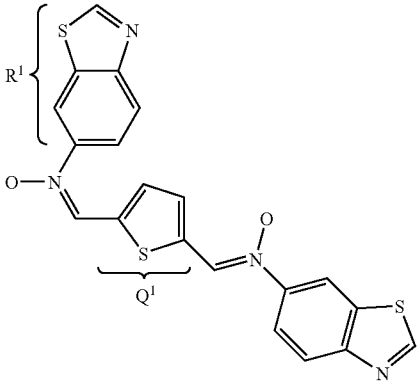 | $R^2$ = hydrogen; a = 2 |

In one embodiment, the present invention photochemically active dye is a the novel thiophene-containing polynitrone having structure (II)

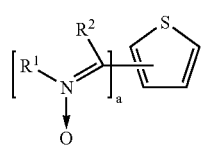

(II)

wherein $R^1$ is independently at each occurrence a $C_1$-$C_{20}$ aliphatic radical, a $C_3$-$C_{20}$ cycloaliphatic radical, or a $C_2$-$C_{30}$ aromatic radical; $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; and "a" is an integer from 2 to 4.

Representative thiophene-containing polynitrones encompassed by generic structure (II) are illustrated in Table II. One of ordinary skill in the art will appreciate the relationship between generic structure (II) and the individual structures of Entries 2a-2e of Table II.

TABLE II
Compounds Exemplifying Thiophene-containing Polynitrones Having Structure (II)
| Entry | Structure | |
|---|---|---|
| 2a | 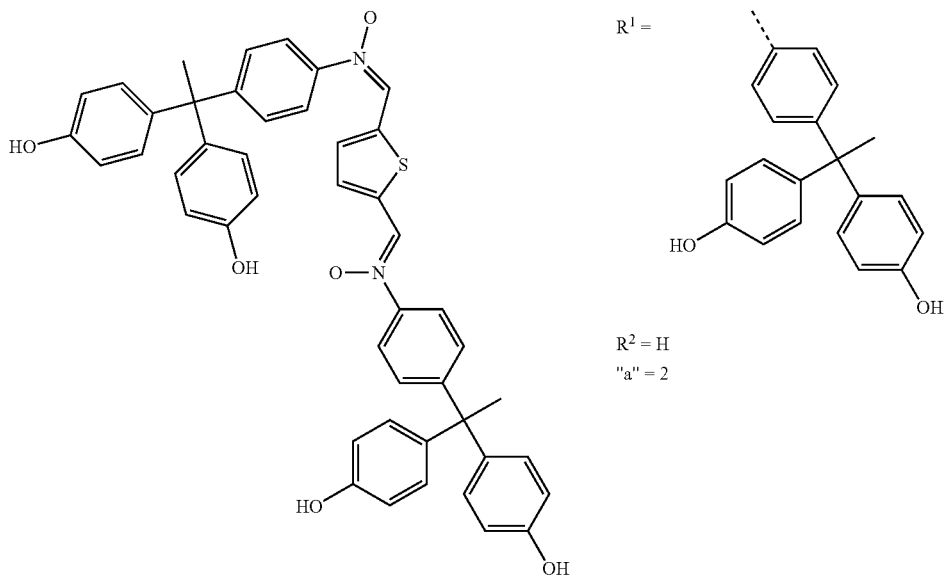 | $R^1$ = <br><br> $R^2$ = H <br> "a" = 2 |
| 2b | 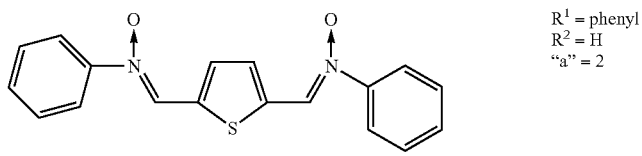 | $R^1$ = phenyl <br> $R^2$ = H <br> "a" = 2 |
| 2c | 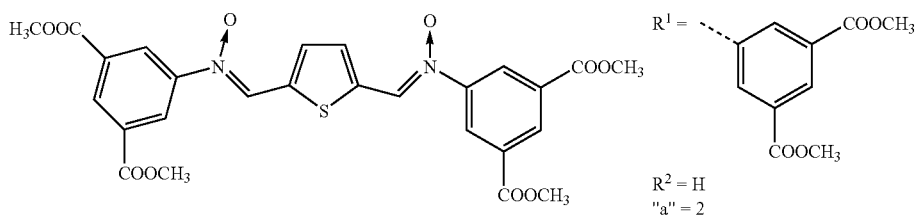 | $R^1$ = <br><br> $R^2$ = H <br> "a" = 2 |
| 2d | 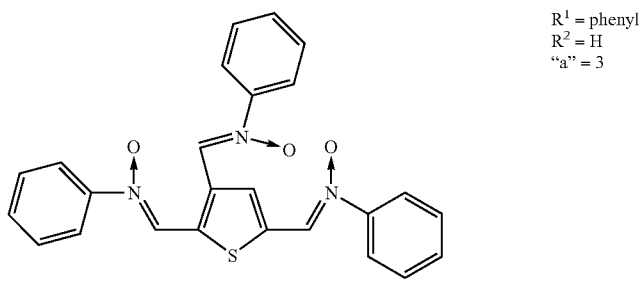 | $R^1$ = phenyl <br> $R^2$ = H <br> "a" = 3 |
| 2e | 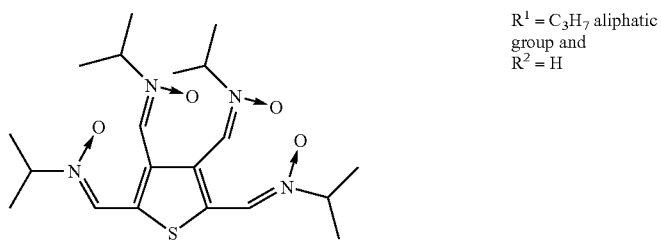 | $R^1 = C_3H_7$ aliphatic group and <br> $R^2$ = H |

In one embodiment, the nitrone moieties (III)

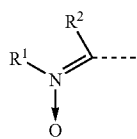
(III)

wherein $R^1$ is a $C_1$-$C_{20}$ aliphatic radical, a $C_3$-$C_{20}$ cycloaliphatic radical, or a $C_2$-$C_{30}$ aromatic radical; and $R^2$ is a hydrogen, a deuterium, a $C_1$-$C_{20}$ aliphatic radical, a $C_3$-$C_{20}$ cycloaliphatic radical, or a $C_2$-$C_{30}$ aromatic radical, are attached to positions 2 and 3, of the thiophene moiety (IV)

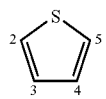
(IV)

In another embodiment, the nitrone moieties (III) are attached to positions 2 and 4, of the thiophene moiety (IV). In yet another embodiment, the nitrone moieties (III) are attached to positions 2 and 5, of the thiophene moiety (IV). In yet another embodiment, the nitrone moieties (III) are attached to positions 3 and 4, of the thiophene moiety (IV).

In another embodiment of the present invention, the photochemically active dye is a novel thiophene-containing dinitrone having structure (V)

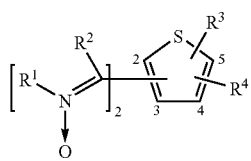
(V)

wherein $R^1$ is independently at each occurrence a $C_1$-$C_{20}$ aliphatic radical, a $C_3$-$C_{20}$ cycloaliphatic radical, or a $C_2$-$C_{30}$ aromatic radical; $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; and $R^3$ and $R^4$ are independently at each occurrence halogen, hydrogen, deuterium, a $C_1$-$C_{20}$ aliphatic radical, a $C_3$-$C_{20}$ cycloaliphatic radical, or a $C_2$-$C_{30}$ aromatic radical.

In one embodiment, the nitrone moieties (III) are attached to positions 2 and 3, of the thiophene moiety (VI)

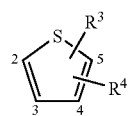
(VI)

wherein $R^3$ and $R^4$ are independently at each occurrence halogen, a hydrogen, a deuterium, a $C_1$-$C_{20}$ aliphatic radical, a $C_3$-$C_{20}$ cycloaliphatic radical, or a $C_2$-$C_{30}$ aromatic radical. In one embodiment, the nitrone moieties (III) are attached to positions 2 and 4, of the thiophene moiety (VI). In another embodiment, the nitrone moieties (III) are attached to positions 2 and 5, of the thiophene moiety (VI). In yet another embodiment, the nitrone moieties (III) are attached to positions 3 and 4, of the thiophene moiety (VI).

In one embodiment, the present invention provides a thiophene-containing dinitrone having structure (VII)

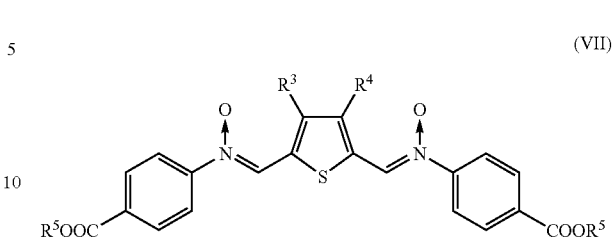
(VII)

wherein $R^3$ and $R^4$ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical; and $R^5$ is independently at each occurrence a $C_1$-$C_{20}$ aliphatic radical, a $C_3$-$C_{20}$ cycloaliphatic radical, or a $C_2$-$C_{30}$ aromatic radical.

In another embodiment, the present invention provides a thiophene-containing dinitrone having structure (VIII)

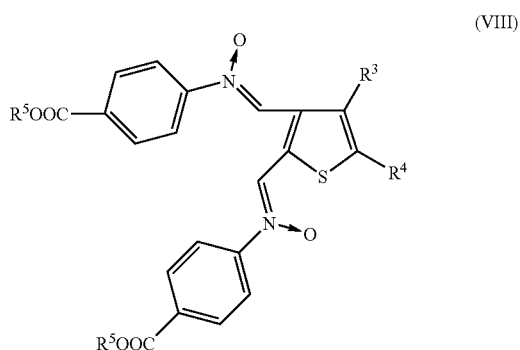
(VIII)

wherein $R^3$ and $R^4$ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical; and $R^5$ is independently at each occurrence a $C_1$-$C_{20}$ aliphatic radical, a $C_3$-$C_{20}$ cycloaliphatic radical, or a $C_2$-$C_{30}$ aromatic radical.

In another embodiment, the present invention provides a thiophene-containing dinitrone having structure (IX).

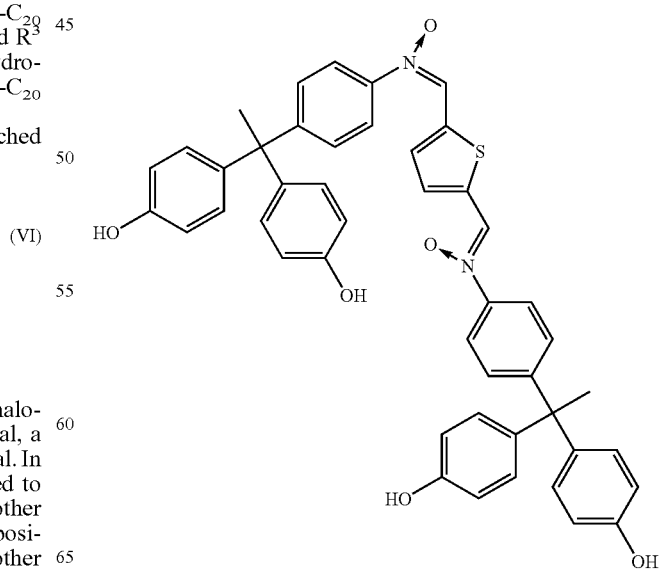
(IX)

The novel thiophene-containing polynitrones and thiophene-containing dinitrones provided by the present invention may be prepared by a variety of methods. In one embodiment, thiophene polynitrones are prepared by contacting a carbonyl compound and a hydroxylamine compound. In one embodiment, the hydroxylamine is a polymer comprising hydroxylamine groups. In one embodiment, the reaction ("contacting") between the carbonyl compound and the hydroxylamine compound can be carried out at room temperature. In an alternate embodiment, the reaction between the carbonyl compound and the hydroxylamine compound can be carried out at a temperature in a range from about 0° C. to about 50° C. In another embodiment, the reaction can be carried out in a solvent at a temperature in excess of 100° C. with the removal of water formed as a by-product in the condensation reaction. In another embodiment, the reaction is carried out in an organic solvent at temperature in a range from about 120° C. to about 160° C. In yet another embodiment, the reaction is carried out in a melt. In certain instances it may be advantageous to conduct the reaction in the presence of a catalyst Suitable solvents include oDCB (orthodichorobenzene), toluene, xylene, chlorobenzene, methylene chloride, anisole, veratrole, alkyl alcohols such as ethanol and methanol, alkanoic acids such as acetic acid, and combinations thereof. The experimental section of this disclosure provides a number of specific methods and conditions for the preparation of novel thiophene-containing polynitrones provided by the present invention.

In one embodiment, the photochemically active dye (sometimes referred to as "the dye") utilized in the present invention has a narrow absorption band, which undergo a chemical change upon exposure to certain "write" wavelengths of light. The photochemically active narrow band dye is defined as having an absorption spectrum which is characterized by a center wavelength associated with the maximum absorption and a spectral width (full width at half of the maximum, FWHM) of less than about 500 nanometers. The photo-product or photo-products which result from interaction of the photochemically active dye with light having the "write" wavelength typically exhibits an absorption spectrum which is entirely different from that exhibited by the dye prior to irradiation. The chemical change in the dye produced by interaction with light of the write wavelength produces a corresponding change in the molecular structure of the dye, thereby producing a "photo-product". This modification to the structure of the dye molecule and concurrent changes in the light absorption properties of the photo-product(s) relative to the starting dye produces a significant change in refractive index within the substrate that can be observed at a "read" wavelength.

In one embodiment, upon exposure to the holographic interference pattern having a first wavelength and intensity sufficient to record at least one optically readable datum, the photoproduct of the photochemically active dye dispersed in an optically transparent substrate comprises an oxaziridine, a rearrangement product of an oxaziridine, or a combination thereof.

In one embodiment, the photoproduct comprises an oxaziridine having structure (X)

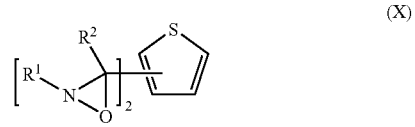

wherein $R^1$ is independently at each occurrence a $C_1$-$C_{20}$ aliphatic radical, a $C_3$-$C_{20}$ cycloaliphatic radical, or a $C_2$-$C_{30}$ aromatic radical; and $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical.

In another embodiment, the photoproduct comprises an oxaziridine having structure (XI)

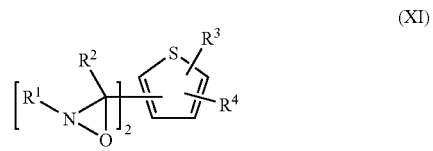

wherein $R^1$ is independently at each occurrence a $C_1$-$C_{20}$ aliphatic radical, a $C_3$-$C_{20}$ cycloaliphatic radical, or a $C_2$-$C_{30}$ aromatic radical; $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; and $R^3$ and $R^4$ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical.

In one embodiment, the photoproduct comprises a mono oxaziridine compound. In some embodiments the photocyclization of the photochemically active polynitrone dye to an oxaziridine photoproduct proceeds with a high quantum efficiency, and a large refractive index change. Typically, the photocyclization is induced in only a portion of the total amount of the photochemically active polynitrone dye present in a given volume element, thus providing a refractive index contrast between the unconverted dye and the oxaziridine photo-product, and providing the concentration variations of the photo-product corresponding to the holographic interference pattern, and constituting the optically readable datum.

In one embodiment, as noted above, step (B) in the method for storing holographic data, comprises irradiating the optically transparent substrate with a holographic interference pattern, wherein the pattern has a first wavelength and an intensity both sufficient to convert, within a volume element of the substrate, at least some of the photochemically active dye into a photo-product, and producing within the irradiated volume element concentration variations of the photo-product corresponding to the holographic interference pattern, thereby producing an optically readable datum corresponding to the volume element. The optically readable datum is stored in the optically transparent substrate as a hologram patterned within at least one volume element of the optically transparent substrate.

Those skilled in the art will appreciate that the lingering photosensitivity of the unconverted (residual) photochemically reactive dye presents a general problem that can adversely affect the integrity of the stored data if no step is taken to stabilize the unconverted photochemically reactive dye. In the case where the unconverted photochemically reactive dye is a polynitrone, protonation of the polynitrone remaining following the recording of the holographic data provides an efficient means of preventing further conversion of the polynitrone to photo-products under the influence of, for example, a read beam or ambient light.

As noted above, a photochemically active dye is disposed on the optically transparent substrate. The photochemically active dye is one, which renders the optically transparent substrate capable of having holograms "written" into it at a first wavelength. And further, the photochemically active dye should be such that a hologram having been "written" into the optically transparent substrate at a first wavelength is not erased when the hologram is "read".

In an embodiment, the optically transparent substrate is irradiated with a holographic interference pattern having a first wavelength to record data. The optically transparent substrate is then irradiated with radiation having a second wavelength to stabilize the written data, and the stabilized data can then be read using radiation having a third wavelength (e.g., a "read beam"), wherein the radiation at each step can independently have a wavelength from about 300 nm to about 1,500 nm. In an embodiment, the first, second, and third wavelengths can be independently between about 300 nm and about 800 nm. In one embodiment, the first wavelength (or the writing wavelength) for writing and recording the data onto the holographic data storage medium is from about 375 nm to about 450 nm. In another embodiment, the first wavelength can be from about 450 nm to about 550 nm. In one embodiment, the first wavelength is in a range from about 375 nm to about 450 nm and the second wavelength is in a range from about 450 to about 1500 nm. In another embodiment, the first wavelength is in a range from about 450 nm to about 550 nm and the second wavelength is in a range from about 550 to about 1500 nm. In still another embodiment, the writing wavelength is such that it is shifted by 0 nm to about 400 nm from the wavelength at which the recorded data is stabilized by the action of light of the second wavelength. Exemplary wavelengths at which writing and data stabilization are accomplished are about 405 nanometers (writing) and about 532 nanometers (stabilization). The first wavelength is also sometimes referred to as the "write" wavelength.

In one embodiment, the photochemically active dye is disposed within the substrate in an amount from about 0.1 weight percent to about 20 weight percent. In some embodiments, the photochemically active dye is present in an amount from about 5 weight percent to about 10 weight percent in the substrate. In yet another embodiment, the photochemically active dye is present in the substrate in an amount from about 15 weight percent to about 20 weight percent. As used herein, the term "weight percent" of the dye refers to a ratio of the weight of the dye included in the substrate to the total weight of the substrate (inclusive of the weight of the dye). For example, 10 weight percent of the dye disposed in a substrate implies 10 grams of the dye in 90 grams of the substrate. The loading percentage of the dye may be controlled to provide desirable properties.

Optically transparent plastic materials may be advantageously employed in the preparation of the optically transparent substrate. Optically transparent plastic materials used in producing holographic data storage media (such as the optically transparent substrate) can comprise any plastic material having sufficient optical quality, e.g., low scatter, low birefringence, and negligible losses at the wavelengths of interest, to render the data in the holographic storage material readable. Organic polymeric materials, such as for example, oligomers, polymers, dendrimers, ionomers, copolymers such as for example, block copolymers, random copolymers, graft copolymers, star block copolymers; and the like, or a combination comprising at least one of the foregoing polymers can be used. Thermoplastic polymers or thermosetting polymers can be used. Examples of suitable thermoplastic polymers include polyacrylates, polymethacrylates, polyamides, polyesters, polyolefins, polycarbonates, polystyrenes, polyesters, polyamideimides, polyaromaticates, polyaromaticsulfones, polyethersulfones, polyphenylene sulfides, polysulfones, polyimides, polyetherimides, polyetherketones, polyether etherketones, polyether ketone ketones, polysiloxanes, polyurethanes, polyaromaticene ethers, polyethers, polyether amides, polyether esters, or the like, or a combination comprising at least one of the foregoing thermoplastic polymers. Some more possible examples of suitable thermoplastic polymers include, but are not limited to, amorphous and semi-crystalline thermoplastic polymers and polymer blends, such as: polyvinyl chloride, linear and cyclic polyolefins, chlorinated polyethylene, polypropylene, and the like; hydrogenated polysulfones, ABS resins, hydrogenated polystyrenes, syndiotactic and atactic polystyrenes, polycyclohexyl ethylene, styrene-acrylonitrile copolymer, styrene-maleic anhydride copolymer, and the like; polybutadiene, polymethylmethacrylate (PMMA), methyl methacrylate-polyimide copolymers; polyacrylonitrile, polyacetals, polyphenylene ethers, including, but not limited to, those derived from 2,6-dimethylphenol and copolymers with 2,3,6-trimethylphenol, and the like; ethylene-vinyl acetate copolymers, polyvinyl acetate, ethylene-tetrafluoroethylene copolymer, aromatic polyesters, polyvinyl fluoride, polyvinylidene fluoride, and polyvinylidene chloride. In one embodiment the optically transparent substrate comprises polycarbonate, for example bisphenol A polycarbonate.

The optically transparent substrate may have a thickness tailored to meet the demands of a particular intended usage of the storage medium. In one embodiment, the thickness of the storage medium is greater than about 100 micrometers. In some embodiments, the thickness may vary from about 100 micrometers to about 5 centimeters. For example, for use as a DVD or CD storage device typical thickness is about 600 micrometers to about 1.2 millimeters. The shape of the optically transparent substrate includes a variety of shapes such as, but not limited to, a square, a rectangle, an oval or a circular shape.

The optically transparent substrate may comprise additional components such as heat stabilizers; antioxidants; light stabilizers; plasticizers; antistatic agents; mold releasing agents; additional resins; binders, blowing agents; and the like, as well as combinations of the foregoing additives.

Generally, the photochemically active polynitrone dyes and polymers used for forming the optically transparent substrate, and the holographic data storage medium should be capable of withstanding the processing conditions used to prepare the holographic data storage medium, for example during a step in which the photochemically active polynitrone and any additional additives which may be present are compounded with a polymer powder and subsequently molded into data storage discs. In various embodiments, the polynitrone dyes provided by the present invention exhibit enhanced thermal stability relative to known photochemically active dyes themselves useful in holographic data storage applications.

In one embodiment, the present invention provides a holographic storage medium comprising an optically transparent substrate comprising a photochemically active polynitrone dye. In an embodiment, a film of an optically transparent substrate comprising an optically transparent plastic material and at least one photochemically active polynitrone dye is formed. Generally, the film is prepared by molding techniques using a molding composition that is obtained by mixing the polynitrone dye with an optically transparent plastic material. Mixing can be conducted in machines such as a single or multiple screw extruder, a Buss kneader, a Henschel, a helicone, an Eirich mixer, a Ross mixer, a Banbury, kneaders, blenders and the like, a roll mill, molding machines such as injection molding machines, vacuum forming machines, blow molding machine, or then like, or a combination comprising at least one of the foregoing machines. Alternatively, the polynitrone dye and the optically transparent plastic material may be dissolved in a solution and films of the optically transparent substrate can be formed from the solution.

In some embodiments, the photochemically active dye is dissolved in a solvent together with the polymer host to produce a solution. Films can be made by spin-coating from this solution. In other embodiments, films can be formed by blade coating, substrate dipping, and spraying the dye/polymer solution. Suitable polymeric substrate materials containing the photochemically active dye are at times referred to as "doped polymers". Such doped polymers can be prepared by a variety of techniques such as the solvent casting technique referred to above. In one embodiment, the doped polymers can also be formed by dissolving the photochemically active dye in a liquid monomer and thereafter thermally or photo-reactively polymerizing the monomer in the presence of the photochemically active dye to produce an optically transparent substrate material having dispersed uniformly within it the photochemically active dye. In another embodiment, such doped polymers is prepared by molding or extrusion techniques of polymer/dye blends.

In one embodiment a data storage composition comprising a photochemically active dinitrone, a thermoplastic polymer is injection molded to form an article that can be used for producing holographic data storage media. The injection-molded article can have any geometry. Examples of suitable geometries include circular discs, square shaped plates, polygonal shapes, or the like. The thickness of the articles can vary, from being at least 100 micrometers in an embodiment, and at least 250 micrometers in another embodiment. A thickness of at least 250 micrometers is useful in producing holographic data storage disks that are comparable to the thickness of current digital storage discs.

The molded data storage medium thus produced can be used for producing data storage articles, which can be used for storing data in the form of holograms. In one embodiment, the molded data storage medium is irradiated with a holographic interference pattern having a first wavelength to record at least one optically readable datum and generate at least one photo-product of the photochemically active dye. The optically readable datum is stored as a hologram patterned within at least one volume element of the data storage medium. Stabilization of the stored data may be achieved by various methods including the post data recording application of a UV screener to the surface of the molded data storage medium. In an embodiment, the stabilized holographic data can be read using radiation having a third wavelength. In an embodiment, this "read wavelength" can be between 350 and 1,100 nm.

The methods disclosed herein can be used for producing holographic data storage media that can be used for bit-wise type data storage in an embodiment, and page-wise type storage of data in another embodiment. In still another embodiment, the methods can be used for storing data in multiple layers of the data storage medium. In view of the various photochemical transformations occurring with the polynitrones during the data recording processes disclosed herein, it becomes possible to identify a holographic data storage medium, or a holographic data storage article comprising such a data storage medium, in terms of the chemical entities present before and after the data storage process. Thus in an embodiment, the present invention provides a holographic data storage medium that can be used for storing data in the form of holograms. Such a data storage medium comprises (i) at least one optically transparent plastic material, and (ii) at least one photochemically active dye.

In another embodiment, the present invention provides a data storage medium comprising (i) at least one optically transparent plastic material, and (ii) at least one photochemically active dye having structure (I). In yet another embodiment, the present invention provides a data storage medium having at least one optically readable datum stored therein, the data storage medium comprising (i) at least one optically transparent plastic material, (ii) at least one photochemically active dye having structure (I), and (iii) at least one photo-stable product derived from the at least one photochemically active dye, or combinations thereof, wherein the at least one optically readable datum is stored as a hologram in the data storage medium.

In another embodiment, the present invention provides a data storage medium comprising (i) at least one optically transparent plastic material, and (ii) at least one photochemically active dye having structure (II). In yet another embodiment another embodiment, the present invention provides a data storage medium having at least one optically readable datum stored therein, the data storage medium comprising (i) at least one optically transparent plastic material, (ii) at least one photochemically active dye having structure (II), and (iii) at least one photo-stable product derived from the at least one photochemically active dye, the at least one photo-product, or combinations thereof, wherein the at least one optically readable datum is stored as a hologram in the data storage medium.

In various embodiments, the read wavelength is different from the write wavelength, such that at the wavelength selected for reading the information contained in the holographic storage medium there is very little or no absorption of the reading light. In one embodiment, the wavelength of light employed for reading is selected such that the difference between the reading wavelength and the absorption band associated with the writing event is maximized. In one embodiment the read beam has a wavelength shifted from about 50 nm to about 400 nm from the write beam's wavelength. In some embodiments, a suitable read beam has a wavelength from about 400 nm to about 800 nm. However, the farther away from the absorption band, the smaller the refractive index change, which negatively impacts the efficiency of the storage process. In addition, the greater the separation between the writing and reading wavelengths, the more difficult it may be to reconstruct the data. Thus, in some embodiments, reading wavelengths are usually selected as the nearest wavelength where the transmission is greater than 95%.

In some embodiments, blue light at wavelengths ranging from about 375 nm to about 425 nm may be used for writing and green/red light at wavelengths ranging from about 500 nm to about 800 nm may be used for reading. In other embodiments, the wavelength of light used for writing can range from about 425 nm to about 550 nm, and the reading wavelength can range from about 600 nm to about 700 nm. In one embodiment, a wavelength of 532 nm light can be used for writing and wavelengths of either 633 nm or 650 nm light can be used for reading.

Additional physical/optical concepts, which will aid one of ordinary skill in the art to better appreciate the methods employed in the development of present invention are included herein. Thus, the absorption cross section is a measurement of an atom or molecule's ability to absorb light at a specified wavelength, and is measured in square cm/molecule. It is generally denoted by $\sigma(\lambda)$ and is governed by the Beer-Lambert Law for optically thin samples as shown in equation (1), $$\sigma(\lambda) = \ln(10) \cdot \frac{\text{Absorbance}(\lambda)}{N_0 \cdot L} (\text{cm}^2) \qquad \text{Equation (1)}$$

wherein $N_0$ is the concentration in molecules per cubic centimeter, and L is the sample thickness in centimeters.

Quantum efficiency (QE) is a measure of the probability of a photochemical transition for each absorbed photon of a given wavelength. Thus, it gives a measure of the efficiency with which incident light is used to achieve a given photochemical conversion, also called as a bleaching process. QE is given by equation (2), $$QE = \frac{hc/\lambda}{\sigma \cdot F_0} \qquad \text{Equation (2)}$$

wherein "h" is the Planck's constant, "c" is the velocity of light, $\sigma(\lambda)$ is the absorption cross section at the wavelength $\lambda$, and $F_0$ is the bleaching fluence. The parameter $F_0$ is given by the product of light intensity (I) and a time constant ($\tau$) that characterizes the bleaching process.

As noted, holographic data storage relies upon the introduction of localized variations in the refractive index of the optically transparent substrate comprising the photochemically active dye as a means of storing holograms. The refractive index within an individual volume element of the optically transparent substrate may be constant throughout the volume element, as in the case of a volume element that has not been exposed to electromagnetic radiation, or in the case of a volume element in which the photochemically active dye has been reacted to the same degree throughout the volume element. It is believed that most volume elements that have been exposed to electromagnetic radiation during the holographic data writing process will contain a complex holographic pattern, and as such, the refractive index within the volume element will vary across the volume element. In instances in which the refractive index within the volume element varies across the volume element, it is convenient to regard the volume element as having an "average refractive index" which may be compared to the refractive index of the corresponding volume element prior to irradiation. Thus, in one embodiment an optically readable datum comprises at least one volume element having a refractive index that is different from a (the) corresponding volume element of the optically transparent substrate prior to irradiation. Data storage is achieved by locally changing the refractive index of the data storage medium in a graded fashion (continuous sinusoidal variations), rather than discrete steps, and then using the induced changes as diffractive optical elements.

As defined herein, the term M/# denotes the capacity of a data storage medium, and can be measured as a function of the total number of multiplexed holograms that can be recorded at a volume element of the data storage medium at a given diffraction efficiency. M/# depends upon various parameters, such as the change in refractive index ($\Delta$n), the thickness of the medium, and the dye concentration. These terms are described further in this disclosure. The M/# is defined as shown in equation (3):

$$M/\# = \sum_{i=1}^{N} \sqrt{\eta i} \qquad \text{Equation (3)}$$

where $\eta_i$ is the diffraction efficiency of the ith hologram, and N is the number of recorded holograms. The experimental setup for M/# measurement for a test sample at a chosen wavelength, for example, at 532 nanometers or 405 nanometers involves positioning the testing sample on a rotary stage that is controlled by a computer. The rotary stage has a high angular resolution, for example, about 0.0001 degree. A M/# measurement involves two steps: recording and readout. At recording, multiple planewave holograms are recorded at the same location on the same sample. A plane wave hologram is a recorded interference pattern produced by a signal beam and a reference beam. The signal and reference beams are coherent to each other. They are both planewaves that have the same power and beam size, incident at the same location on the sample, and polarized in the same direction. Multiple planewave holograms are recorded by rotating the sample. Angular spacing between two adjacent holograms is about 0.2 degree. This spacing is chosen so that their impact to the previously recorded holograms, when multiplexing additional holograms, is minimal and at the same time, the usage of the total capacity of the media is efficient. Recording time for each hologram is generally the same in M/# measurements. At readout, the signal beam is blocked. The diffracted signal is measured using the reference beam and an amplified photo-detector. Diffracted power is measured by rotating the sample across the recording angle range with a step size of about 0.004 degree. The power of the reference beam used for readout is typically about 2-3 orders of magnitude smaller than that used at recording. This is to minimize hologram erasure during readout while maintaining a measurable diffracted signal. From the diffracted signal, the multiplexed holograms can be identified from the diffraction peaks at the hologram recording angles. The diffraction efficiency of the ith hologram, $\eta_i$, is then calculated by using equation (4):

$$\eta i = \frac{P_{i, diffracted}}{P_{reference}} \quad \text{Equation (4)}$$

where $P_{i, diffracted}$ is the diffracted power of the ith hologram. M/# is then calculated using the diffraction efficiencies of the holograms and equation (3). Thus, a holographic plane wave characterization system may be used to test the characteristics of the data storage material, especially multiplexed holograms. Further, the characteristics of the data storage material can also be determined by measuring the diffraction efficiency.

The capacity to store data as holograms (M/#) is also directly proportional to the ratio of the change in refractive index per unit dye density (Δn/N0) at the wavelength used for reading the data to the absorption cross section (σ) at a given wavelength used for writing the data as a hologram. The refractive index change per unit dye density is given by the ratio of the difference in refractive index of the volume element before irradiation minus the refractive index of the same volume element after irradiation to the density of the dye molecules. The refractive index change per unit dye density has a unit of (centimeter)³. Thus in an embodiment, the optically readable datum comprises at least one volume element wherein the ratio of the change in the refractive index per unit dye density of the at least one volume element to an absorption cross section of the at least one photochemically active dye is at least about 10-5 expressed in units of centimeter.

Sensitivity (S) is a measure of the diffraction efficiency of a hologram recorded using a certain amount of light fluence (F). The light fluence (F) is given by the product of light intensity (I) and recording time (t). Mathematically, sensitivity is given by equation (5), $$S = \frac{\sqrt{\eta}}{I \cdot t \cdot L} (cm/J) \quad \text{Equation (5)}$$

wherein I is the intensity of the recording beam, "t" is the recording time, L is the thickness of the recording (or data storage) medium (example, disc), and η is the diffraction efficiency. Diffraction efficiency is given by equation (6), $$\eta = \sin^2 \frac{\pi \cdot \Delta n \cdot L}{\lambda \cdot \cos(\theta)} \quad \text{Equation (6)}$$

wherein λ is the wavelength of light in the recording medium, θ is the recording angle in the media, and Δn is the refractive index contrast of the grating, which is produced by the recording process, wherein the dye molecule undergoes a photochemical conversion.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. The following examples are intended only to illustrate methods and embodiments in accordance with the invention, and as such should not be construed as imposing limitations upon the claims.

EXAMPLES

Proton NMR spectra was measured using a 300 megahertz Bruker NMR spectrometer and $d_6$-dimethylsulfoxide or $CDCl_3$ as solvent. Compounds were further characterized by a liquid chromatograph-mass spectrometer (LC-MS) system, comprising a liquid chromatograph and a Quattro Ultima Pt mass spectrometer. An Xterra C18 (50 mm×4.6 mm; 5 microns) column was used for the separating the components by liquid chromatography. The separated components were then analyzed by mass spectrometry. Ultraviolet-visible (UV-VIS) spectra were recorded using a double beam Perkin-Elmer Lambda 900 UV-VIS-NIR spectrophotometer. Differential Scanning Chromatography (DSC) experiments were performed to study the thermal behavior of nitrones especially for melting or decomposition temperature. The melting or decomposition temperatures were measured in presence of nitrogen with a heating rate of 10° C./minute using DSCQ10 (TA) instrument Preparation of 4-Carbethoxyphenylhydroxylamine 1

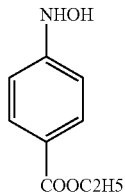

A solution of ethyl p-nitro benzoate (14.6 gm, 75 mmol) in 95% ethanol (75 ml) was mixed with ammonium chloride (4.6 gm, 86 mmol) in water (70 ml) in 250 ml 3-necked flask. The resulting milky suspension was cooled on an ice bath and treated with zinc dust (10.9 gm, 167 mmol) in portions with stirring to keep the reaction mixture below 35° C. After about two and half hours the zinc oxide was removed by filtration and rinsed with hot water followed by methylene chloride. The aqueous filtrate was once again extracted with methylene chloride, and the combined methylene chloride extracts were washed with brine, dried over anhydrous sulphate and evaporated under reduced pressure. An orange oil was thus obtained (11.6 gm, 64 mmol, 85%). The crystallization of the oily product gave 5.6 gm (~42% yield) purified 4-carbethoxyphenylhydroxylamine (HPLC purity of 95.9% and a melting point of 72.5° C.).

Example 1

Preparation of 2,5-Bis(N-(4-Ethoxycarbonylphenyl) Imino-N-Oxide) Thiophene Ex. 1

Ex. 1

C₂H₅OOC—⟨phenyl⟩—N(→O)=CH—⟨thiophene⟩—CH=N(→O)—⟨phenyl⟩—COOC₂H₅

Carbethoxyphenylhydroxylamine 1 (3.36 gm, 18.5 mmol) was mixed with 2,5 thiophenedicarboxaldehyde (0.65 gm, 4.64 mmol) in glacial acetic acid (70 ml) and stirred at room temperature for 20 hours. The reaction mixture was poured into water (200 ml) and the product was filtered. The filtered product was washed with water and dried at 60° C. to give 2.0 gm orange colored crude product. The product was purified by boiling the crude product in acetonitrile followed by filtration gave 1.0 gm (~46.0% yield) 2,5-bis(N-(4-ethoxycarbonylphenyl) imino-N-oxide) thiophene (HPLC purity: 94.3%; DSC: 247° C.).

Preparation of 4-Nitro-Benzoic Acid 2-Ethyl-Hexyl Ester 2

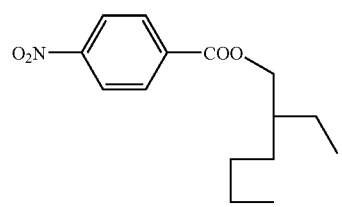

2

To the 250 ml 3-necked flask was added 10.0 gm 2-ethyl 1-hexanol, 100 ml dichloromethane, and 6.0 gm pyridine and the contents were stirred for 10 minutes. To this mixture, 14.2 gm 4-nitro benzoyl chloride was added slowly and stirred under reflux conditions for 2 hrs. The reaction mixture was then cooled, washed with 20% aqueous ammonium hydroxide. The organic layer was washed with 1N hydrochloric acid and brine, and dried over anhydrous sodium sulfate to give a crude product (~65% yield).

Preparation of 4-Hydroxyamino-Benzoic Acid 2-Ethyl-Hexyl Ester 3

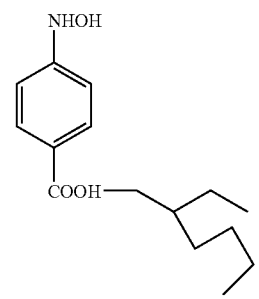

3

To a 500 ml 3-necked flask was added 14 gm p-nitro phenyl 2 ethyl hexyl ester, 50 ml ethanol, 3.1 gm ammonium chloride, and 50 ml water. To this mixture 7.3 gm zinc was added slowly and stirred at room temperature for 5 hrs. The mixture was washed with methylenedichloride (MDC), that separated the organic layer. After distillation of MDC, solid was obtained in a yield of 5.6 gm (42%).

Example 2

Preparation of 2,5-Thiophene Bis-2-Ethylhexylesterphenyl Dinitrone (Ex. 2)

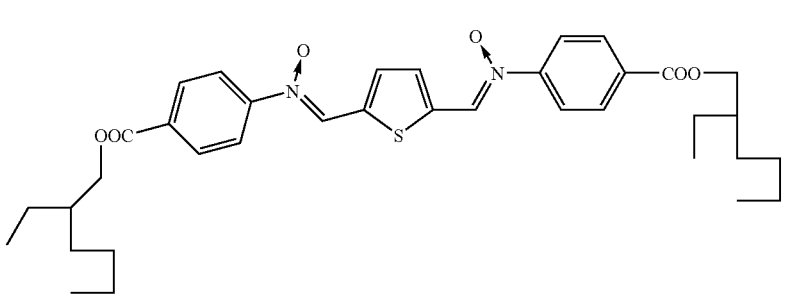

Ex.2

To a 250 ml 3-necked flask was added 0.5 gm 2,5-thiophenedicarboxaldehyde, 30 ml acetic acid, 5.6 gm 2-ethylhexylesterphenyl hydroxylamine 3 and stirred for 20 hrs at room temperature. To the reaction mixture, 100 ml water was added and the mixture was filtered. The filtered product was washed with water and dried. A yield of about 1.6 gm of 2,5-thiophene bis-2-ethylhexylesterphenyl dinitrone of Ex. 2 was obtained with a HPLC purity of 98% (DSC: 205° C.).

Structures of the various nitrone and dinitrone dyes studied are gathered in Table 1 together with data for diffraction efficiency and quantum efficiency measured for molded disks containing the dye. In addition data on nitrone stability is also presented.

der. The disk was molded in a small injection molding machine (Mini-jector) a 10 ton vertical injection machine, with a polished mold surface and mirrored stamper at a barrel temperature of about 200-210° C. to produce disks of 1.2 mm thickness and a diameter of 5.8 cm.

Diffraction efficiency was measured for the disk of Comparative Example 2 and Example 3 as follows. A standard experimental setup was used to measure diffraction efficiency in a transmission geometry at a wavelength of 532 nm. Similar characterization was also carried out at 405 nm. For the sensitivity measurements, both the reference beam and the

TABLE 1

| | Dye Structure | Diffraction Efficiency at 532 nm write/read | Quantum Efficiency At 532 nm | Decomposition Temprature (° C.) |
|---|---|---|---|---|
| CEx. 1 | | — | 0.0 | 110 |
| CEx. 2 | | 0.09 | 0.05 | 185 |
| CEx. 3 | | — | — | 80 |
| Ex. 3 | | 0.42 | 0.18 | 247 |
| Ex. 4 | | — | — | 251 |
| Ex. 5 | | — | — | 210 |

Molded disks containing the nitrone or dinitrone dye were prepared as follows. Molded disk for testing were prepared using a blend of polystyrene (PS1301) pellets that were ground to a coarse powder in a Retsch mill and dried in a circulating air oven at 80° C. for at least 4 hours. In a Henschel mixer, 150 g of the dry polystyrene and 0.9 g of the dye (as given in Table 1) were blended to form a homogeneous powsignal beam were incident on the test sample at oblique angles of 45° for hologram recording. The sample was positioned on a rotary stage, which was controlled by a computer. Both the reference and signal beams had the same optical power and were polarized in the same direction (parallel to the sample surface). The beam diameters ($1/e_2$) were 4 mm. A color filter and a small pinhole were placed in front of the detector to reduce optical noise from background light. A fast mechanical shutter in front of the laser controlled the hologram recording time. In the 532 nm setup, a red 632 nm beam was used to monitor the dynamics during hologram recording. The recording power for each beam varied from 1 mW to 100 mW and the recording time varied from 10 ms to a few seconds. The diffracted power from a recorded hologram was determined from a Bragg detuning curve by rotating the sample disc by 0.2-0.4 degrees. The power used to read out the holograms was two to three orders of magnitude lower than the recording power in order to minimize hologram erasure during readout.

Quantum efficiencies were measured for Example 3 and Comparative Examples 1 and 2 as follows Samples of known thickness and concentration with absorption of about 0.2 at the measurement wavelength were prepared. The absorption spectrum of the sample was measured from 200 to 900 nm. The sample thickness, laser power and the laser spot size at the sample surface were measured A bleaching experiment was then performed on the sample to obtain the instantaneous bleaching fluence $F_0$ at the wavelength of interest while the UV vis spectrum from 200 to 900 nm was measured in short time intervals (0.1 s to 1 s). The bleaching process was followed by monitoring the absorption at a suitable wavelength different from the exposure wavelength. A standard experimental setup for measuring quantum efficiency was employed. The sample was exposed at the same spot where the UV vis was measured with a uniform light beam of known intensity I and spot size. Typically, the samples were illuminated until the bleaching process was complete, as indicated by a steady state. The transmitted power P(t) during exposure follows an exponential decay curve when the absorption of the sample is relatively low.

The absorption cross-section was calculated according to equation 1 and the quantum efficiency according to equation 2.

The thermal stability of a holographic data storage medium may at times be a critical characteristic for long-term reliability. When the fabrication occurs via a molding process, the importance of thermal stability of the dye is even greater as molding temperatures may exceed 200° C. In order for the dye to remain intact during all processing steps of the media fabrication, its decomposition temperature needs to be above the processing temperatures. The thermal stability of dyes is typically evaluated in a DSC experiment.

The quantum efficiency (QE) of the photo-rearrangement of a dye is directly related to its sensitivity. The higher the QE, the higher the sensitivity can be. A higher sensitivity of the data storage medium allows for faster write times. Furthermore, if the photo-rearrangement of the dye has a low QE, much of the energy deposited in the material is converted into heat, which can have detrimental effects on the grating writing process. The diffraction efficiency that can be obtained in a holographic data storage medium is a measure for its data storage capacity. Same applications require high DE in order to function. In all cases, however, a high DE is advantageous.

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied, those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

The invention claimed is:

1. A thiophene-containing polynitrone compound having structure (II)

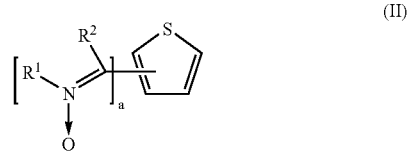

wherein $R^1$ is independently at each occurrence a structure having a formula:

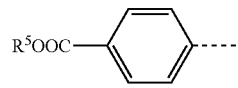

$R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; $R^5$ is independently at each occurrence a $C_1$-$C_{20}$ aliphatic radical, a $C_3$-$C_{20}$ cycloaliphatic radical, or a $C_2$-$C_{30}$ aromatic radical; and "a" is an integer from 2 to 4.

2. The polynitrone of claim 1, wherein the nitrone moieties

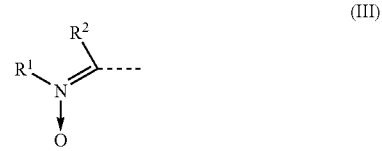

are attached at positions 2 and 3 of the thiophene moiety

wherein $R^1$ is independently at each occurrence a structure having a formula:

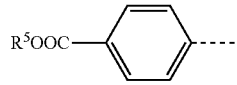  (5)

$R^5$ is independently at each occurrence a $C_1$-$C_{20}$ aliphatic radical, a $C_3$-$C_{20}$ cycloaliphatic radical, or a $C_2$-$C_{30}$ aromatic radical; and $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical.

3. The polynitrone of claim 1, wherein the nitrone moieties

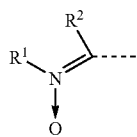  (III)

are attached at positions 2 and 4 of the thiophene moiety

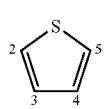  (IV)

wherein $R^1$ is independently at each occurrence a structure having a formula:

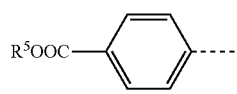  (5)

$R^5$ is independently at each occurrence a $C_1$-$C_{20}$ aliphatic radical, a $C_3$-$C_{20}$ cycloaliphatic radical, or a $C_2$-$C_{30}$ aromatic radical; and $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical.

4. The polynitrone of claim 1, wherein the nitrone moieties

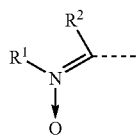  (III)

are attached at positions 2 and 5 of the thiophene moiety

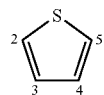  (IV)

wherein $R^1$ is independently at each occurrence a structure having a formula:

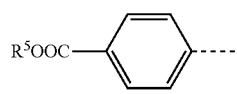  (5)

$R^5$ is independently at each occurrence a $C_1$-$C_{20}$ aliphatic radical, a $C_3$-$C_{20}$ cycloaliphatic radical, or a $C_2$-$C_{30}$ aromatic radical; and $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical.

5. The polynitrone of claim 1, wherein the nitrone moieties

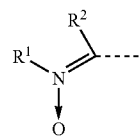  (III)

are attached at positions 3 and 4 of the thiophene moiety

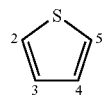  (IV)

wherein $R^1$ is independently at each occurrence a structure having a formula:

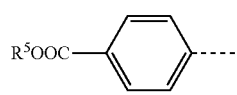  (5)

$R^5$ is independently at each occurrence a $C_1$-$C_{20}$ aliphatic radical, a $C_3$-$C_{20}$ cycloaliphatic radical, or a $C_2$-$C_{30}$ aromatic radical; and $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical.

6. An article comprising the polynitrone of claim 1.

7. A photo-product of the polynitrone of claim 1.

8. The photoproduct of claim 7 comprising an oxaziridine having structure (X)

(X)

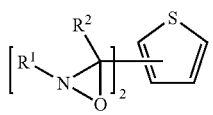

wherein R¹ is independently at each occurrence a structure having a formula:

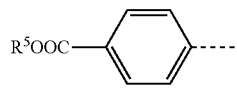

R⁵ is independently at each occurrence a $C_1$-$C_{20}$ aliphatic radical, a $C_3$-$C_{20}$ cycloaliphatic radical, or a $C_2$-$C_{30}$ aromatic radical; and R² is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical.

9. A thiophene-containing dinitrone compound having structure (V)

(V)

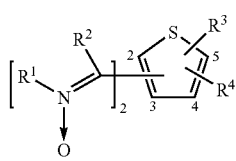

wherein R¹ is independently at each occurrence a structure having a formula:

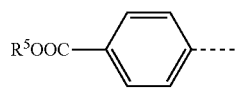

R² is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; R⁵ is independently at each occurrence a $C_1$-$C_{20}$ aliphatic radical, a $C_3$-$C_{20}$ cycloaliphatic radical, or a $C_2$-$C_{30}$ aromatic radical; and R³ and R⁴ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical.

10. The dinitrone of claim 9, wherein the nitrone moieties (III)

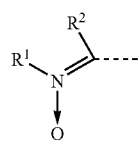

are attached at positions 2 and 3 of the thiophene moiety (VI)

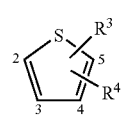

wherein R¹ is independently at each occurrence a structure having a formula:

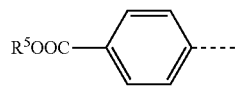

R² is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; R⁵ is independently at each occurrence a $C_1$-$C_{20}$ aliphatic radical, a $C_3$-$C_{20}$ cycloaliphatic radical, or a $C_2$-$C_{30}$ aromatic radical; and R³ and R⁴ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical.

11. The dinitrone of claim 9, wherein the nitrone moieties (III)

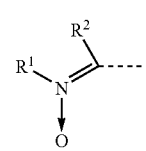

are attached at positions 2 and 4 of the thiophene moiety (VI)

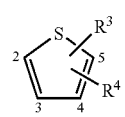

wherein R¹ is independently at each occurrence a structure having a formula:

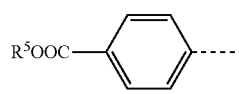

R² is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; R⁵ is independently at each occurrence a $C_1$-$C_{20}$ aliphatic radical, a $C_3$-$C_{20}$ cycloaliphatic radical, or a $C_2$-$C_{30}$ aromatic radical; and R³ and R⁴ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical.

12. The dinitrone of claim 9, wherein the nitrone moieties

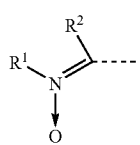
(III)

are attached at positions 2 and 5 of the thiophene moiety

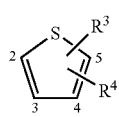
(VI)

wherein $R^1$ is independently at each occurrence a structure having a formula:

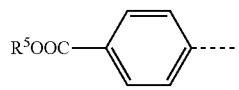

$R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; and $R^3$ and $R^4$ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical.

13. The dinitrone of claim 9, wherein the nitrone moieties

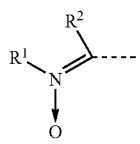
(III)

are attached at positions 3 and 4 of the thiophene moiety

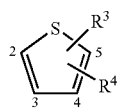
(VI)

wherein $R^1$ is independently at each occurrence a structure having a formula:

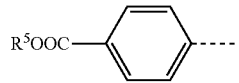

$R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; $R^5$ is independently at each occurrence a $C_1$-$C_{20}$ aliphatic radical, a $C_3$-$C_{20}$ cycloaliphatic radical, or a $C_2$-$C_{30}$ aromatic radical; and $R^3$ and $R^4$ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical.

14. The composition of claim 9, where in the dinitrone compound has a structure (VII)

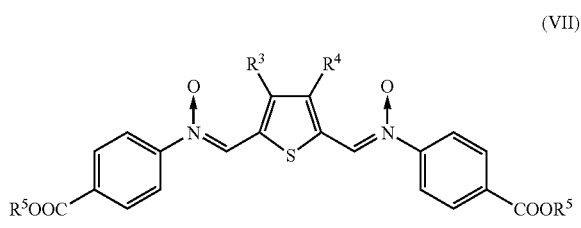
(VII)

wherein $R^3$ and $R^4$ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical; and $R^5$ is independently at each occurrence a $C_1$-$C_{20}$ aliphatic radical, a $C_3$-$C_{20}$ cycloaliphatic radical, or a $C_2$-$C_{30}$ aromatic radical.

15. The composition of claim 1, where in the dinitrone compound has a structure (VIII)

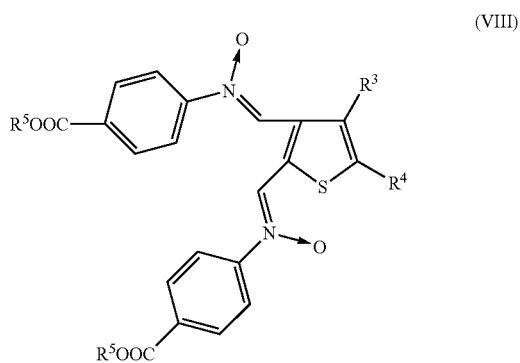
(VIII)

wherein $R^3$ and $R^4$ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical; and $R^5$ is independently at each occurrence a $C_1$-$C_{20}$ aliphatic radical, a $C_3$-$C_{20}$ cycloaliphatic radical, or a $C_2$-$C_{30}$ aromatic radical.

16. An article comprising the dinitrone of claim 9.

17. A photo-product of the dinitrone of claim 9.

18. The photoproduct of claim 17 comprising structure (XI)

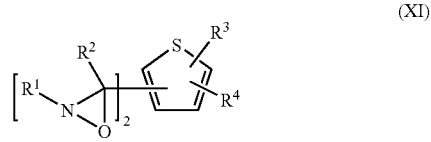
(XI)

wherein $R^1$ is independently at each occurrence a structure having a formula:

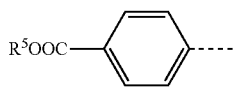

$R^5$ is independently at each occurrence a $C_1$-$C_{20}$ aliphatic radical, a $C_3$-$C_{20}$ cycloaliphatic radical, or a $C_2$-$C_{30}$ aromatic radical; $R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; and $R^3$ and $R^4$ are independently halogen, hydrogen, deuterium, a $C_1$-$C_{20}$ aliphatic radical, a $C_3$-$C_{20}$ cycloaliphatic radical, or a $C_2$-$C_{30}$ aromatic radical.

19. A method for the preparation of a thiophene-containing polynitrone compound having structure (II),

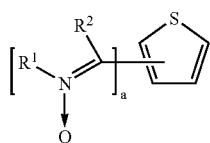

(II)

wherein $R^1$ is independently at each occurrence a structure having a formula:

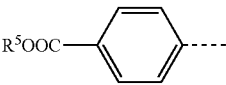

$R^2$ is independently at each occurrence hydrogen, deuterium, a $C_1$-$C_{20}$ aliphatic radical, a $C_3$-$C_{20}$ cycloaliphatic radical, or a $C_2$-$C_{30}$ aromatic radical; $R^5$ is independently at each occurrence a $C_1$-$C_{20}$ aliphatic radical, a $C_3$-$C_{20}$ cycloaliphatic radical; and "a" is an integer from 2 to 4; said method comprising contacting a carbonyl compound with a hydroxylamine compounds in a solvent at a temperature in a range between about 0° C. and about 50° C.

20. The method according to claim 19, wherein said solvent comprises acetic acid.

* * * * *